United States Patent [19]
Sasnett, Sr.

[11] Patent Number: 6,098,232
[45] Date of Patent: Aug. 8, 2000

[54] HAND AND FINGER NAIL WASH UNIT

[76] Inventor: Marvin E. Sasnett, Sr., P.O. Box 95246, Oklahoma City, Okla. 73143

[21] Appl. No.: 09/405,660

[22] Filed: Sep. 24, 1999

[51] Int. Cl.$^7$ .............................. A47L 25/00; A46B 15/00
[52] U.S. Cl. ........................... 15/104.92; 15/21.1; 132/73
[58] Field of Search ................................. 15/167.3, 21.1, 15/104.92; 132/73

[56] References Cited

U.S. PATENT DOCUMENTS 3,439,370  4/1969  McLaughlin ............................. 15/21.1

*Primary Examiner*—Randall E. Chin

[57] ABSTRACT

A hand and finger nail wash unit for all types of workplace environments. The hand and finger nail wash unit includes a housing having a front side, a back side, a top side, a first opposing wall, a second opposing wall, and a bottom portion. A compartment in the housing holds a water pump and is formed by a vertical wall within an interior of the housing and the first opposing wall. An aperture is in the front side for access to an interior of the housing. A brush for cleaning nails is mounted on an inside surface of the bottom portion of the housing. A water pump is in the compartment. The water pump has an intake pump for receiving water from the housing. The intake pipe is fluidly connected with a first bore in the vertical wall. The water pump has and outlet pipe for directing water from the pump into the housing. The outlet pipe is fluidly connected to a second bore in the vertical wall. A pipe for delivering water into the housing is fluidly connected to the second bore. The pipe has bores therein for directing water out of the pipe.

13 Claims, 3 Drawing Sheets

HAND AND FINGER NAIL WASH UNIT

BACKGROUND OF THE INVENTION

1. Field of the Invention

The present invention relates to hand washing units and more particularly pertains to a new hand and finger nail wash unit for all types of workplace environments.

2. Description of the Prior Art

The use of hand washing units is known in the prior art. More specifically, hand washing units heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. Nos. 4,388,585; 5,265, 628; 4,769,863; 5,727,579; 4,219,637; and U.S. Pat. Des. No. 272,263.

While these devices fulfill their respective, particular objectives and requirements, the aforementioned patents do not disclose a new hand and finger nail wash unit. The inventive device includes a housing having a front side, a back side, a top side, a first opposing wall, a second opposing wall, and a bottom portion. A compartment in the housing holds a water pump and is formed by a vertical wall within an interior of the housing and the first opposing wall. An aperture is in the front side for access to an interior of the housing. A brush for cleaning nails is mounted on an inside surface of the bottom portion of the housing. A water pump is in the compartment. The water pump has an intake pump for receiving water from the housing. The intake pipe is fluidly connected with a first bore in the vertical wall. The water pump has and outlet pipe for directing water from the pump into the housing. The outlet pipe is fluidly connected to a second bore in the vertical wall. A pipe for delivering water into the housing is fluidly connected to the second bore. The pipe has bores therein for directing water out of the pipe.

In these respects, the hand and finger nail wash unit according to the present invention substantially departs from the conventional concepts and designs of the prior art, and in so doing provides an apparatus primarily developed for the purpose of all types of workplace environments.

SUMMARY OF THE INVENTION

In view of the foregoing disadvantages inherent in the known types of hand washing units now present in the prior art, the present invention provides a new hand and finger nail wash unit construction wherein the same can be utilized for all types of workplace environments.

The general purpose of the present invention, which will be described subsequently in greater detail, is to provide a new hand and finger nail wash unit apparatus and method which has many of the advantages of the hand washing units mentioned heretofore and many novel features that result in a new hand and finger nail wash unit which is not anticipated, rendered obvious, suggested, or even implied by any of the prior art hand washing units, either alone or in any combination thereof.

To attain this, the present invention generally comprises includes a housing having a front side, a back side, a top side, a first opposing wall, a second opposing wall, and a bottom portion. A compartment in the housing holds a water pump and is formed by a vertical wall within an interior of the housing and the first opposing wall. An aperture is in the front side for access to an interior of the housing. A brush for cleaning nails is mounted on an inside surface of the bottom portion of the housing. A water pump is in the compartment. The water pump has an intake pump for receiving water from the housing. The intake pipe is fluidly connected with a first bore in the vertical wall. The water pump has and outlet pipe for directing water from the pump into the housing. The outlet pipe is fluidly connected to a second bore in the vertical wall. A pipe for delivering water into the housing is fluidly connected to the second bore. The pipe has bores therein for directing water out of the pipe.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new hand and finger nail wash unit apparatus and method which has many of the advantages of the hand washing units mentioned heretofore and many novel features that result in a new hand and finger nail wash unit which is not anticipated, rendered obvious, suggested, or even implied by any of the prior art hand washing units, either alone or in any combination thereof.

It is another object of the present invention to provide a new hand and finger nail wash unit which may be easily and efficiently manufactured and marketed.

It is a further object of the present invention to provide a new hand and finger nail wash unit which is of a durable and reliable construction.

An even further object of the present invention is to provide a new hand and finger nail wash unit which is susceptible of a low cost of manufacture with regard to both materials and labor, and which accordingly is then susceptible of low prices of sale to the consuming public, thereby making such hand and finger nail wash unit economically available to the buying public.

Still yet another object of the present invention is to provide a new hand and finger nail wash unit which provides in the apparatuses and methods of the prior art some of the advantages thereof, while simultaneously overcoming some of the disadvantages normally associated therewith.

Still another object of the present invention is to provide a new hand and finger nail wash unit for all types of workplace environments.

Yet another object of the present invention is to provide a new hand and finger nail wash unit which includes a housing having a front side, a back side, a top side, a first opposing wall, a second opposing wall, and a bottom portion. A compartment in the housing holds a water pump and is formed by a vertical wall within an interior of the housing and the first opposing wall. An aperture is in the front side for access to an interior of the housing. A brush for cleaning nails is mounted on an inside surface of the bottom portion of the housing. A water pump is in the compartment. The water pump has an intake pump for receiving water from the housing. The intake pipe is fluidly connected with a first bore in the vertical wall. The water pump has and outlet pipe for directing water from the pump into the housing. The outlet pipe is fluidly connected to a second bore in the vertical wall. A pipe for delivering water into the housing is fluidly connected to the second bore. The pipe has bores therein for directing water out of the pipe.

Still yet another object of the present invention is to provide a new hand and finger nail wash unit that can be hooked up to an external water supply for using continuously fresh water.

Even still another object of the present invention is to provide a new hand and finger nail wash unit that can be used by everyone regardless of the medium, which requires removal from the hands and fingernails.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
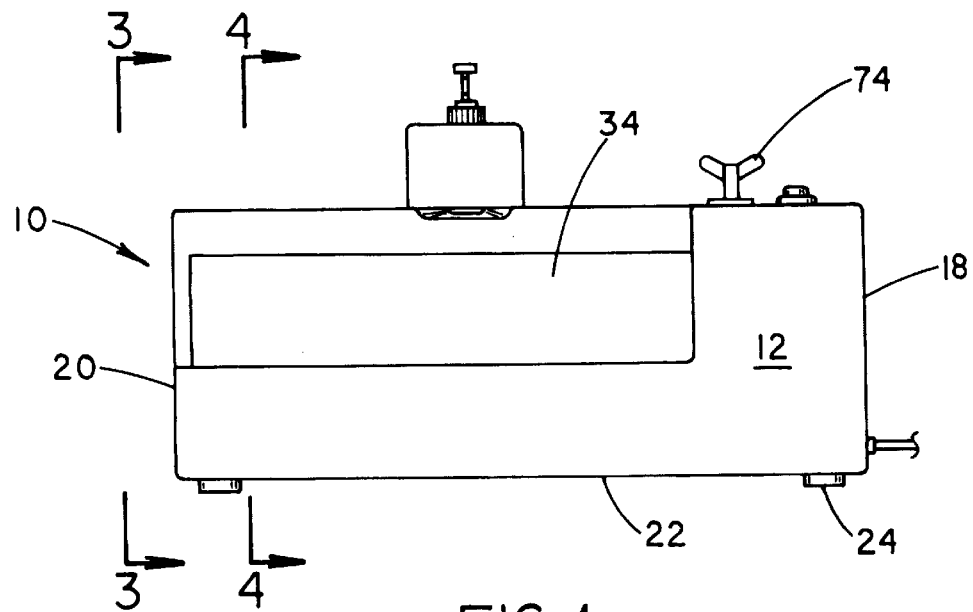
FIG. 1 is a schematic front view of a new hand and finger nail wash unit according to the present invention.
Figure 2:
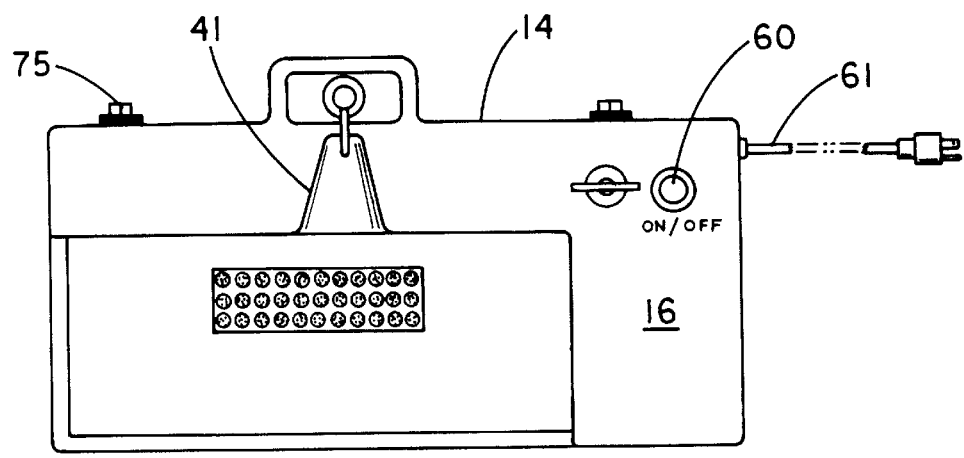
FIG. 2 is a schematic top view of the present invention.
Figure 3:
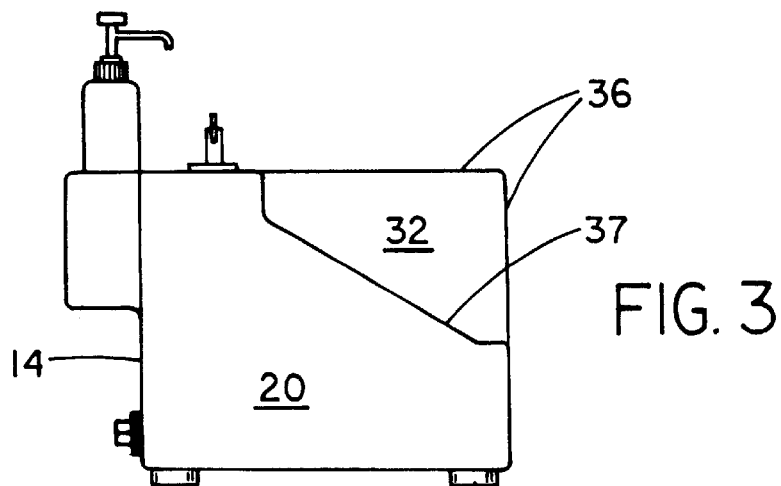
FIG. 3 is a schematic side view of the present invention.
Figure 4:
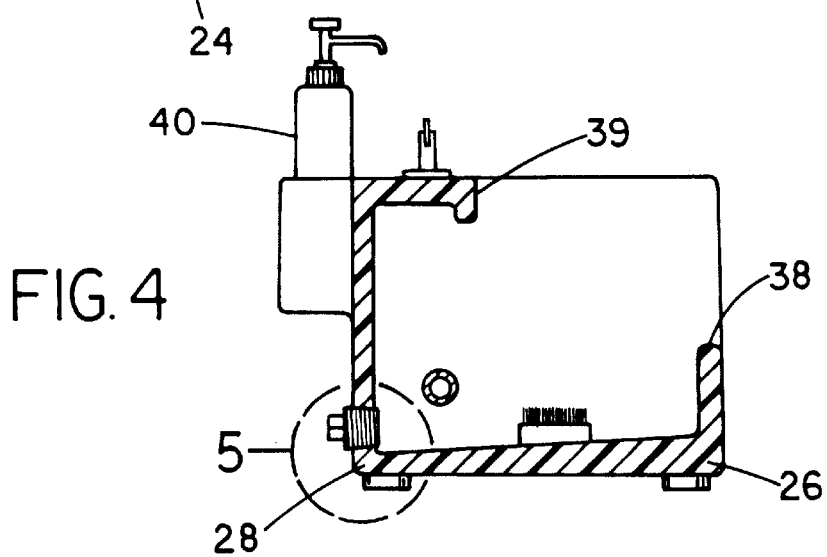
FIG. 4 is a schematic side plan cross-sectional view of the present invention.
Figure 5:
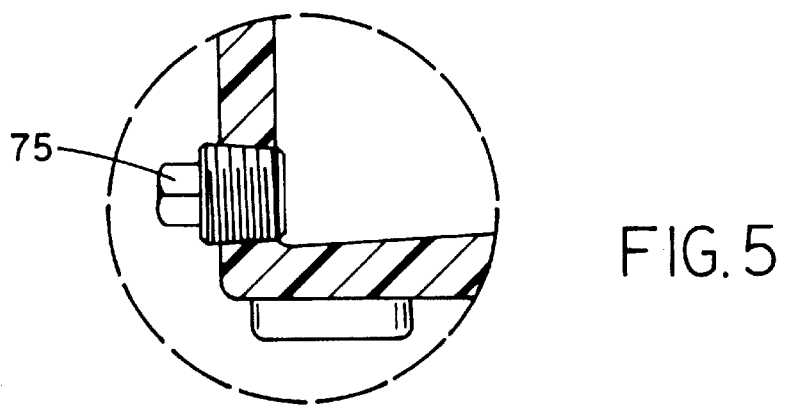
FIG. 5 is a schematic exploded view of the drain hole of the present invention.
Figure 6:
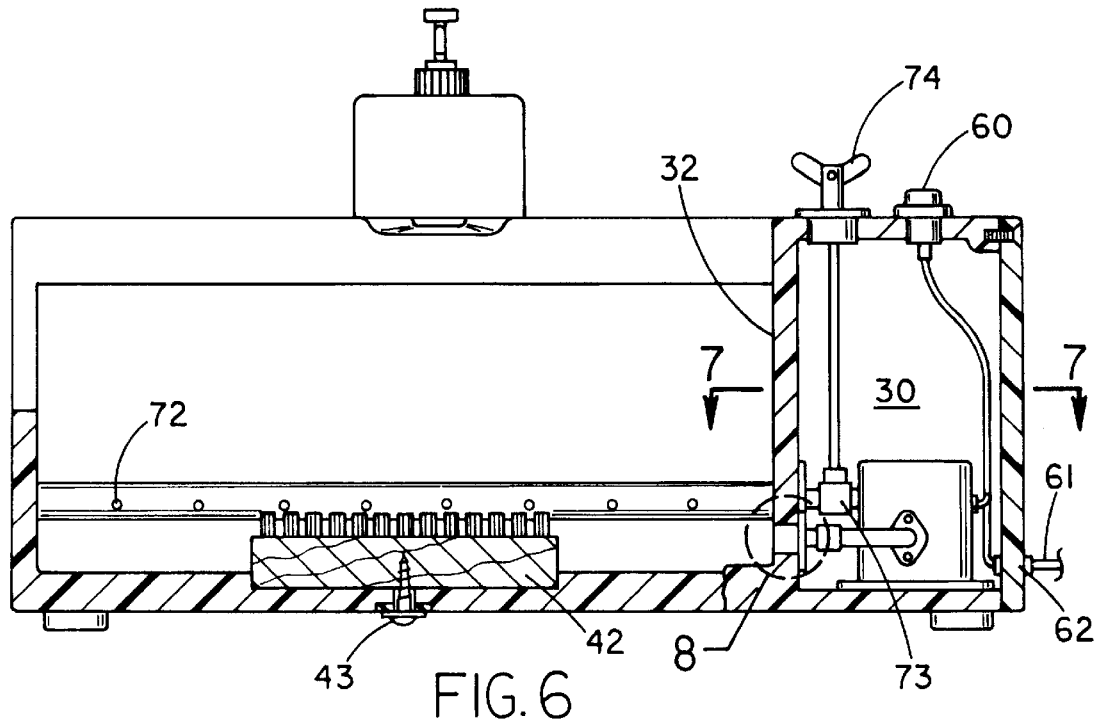
FIG. 6 is a schematic front plan view of the present invention.
Figure 8:
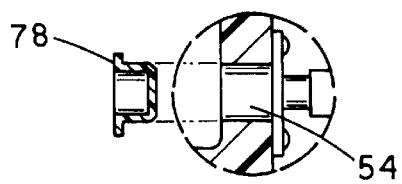
FIG. 8 is a schematic exploded view of the first bore of the present invention.
Figure 7:
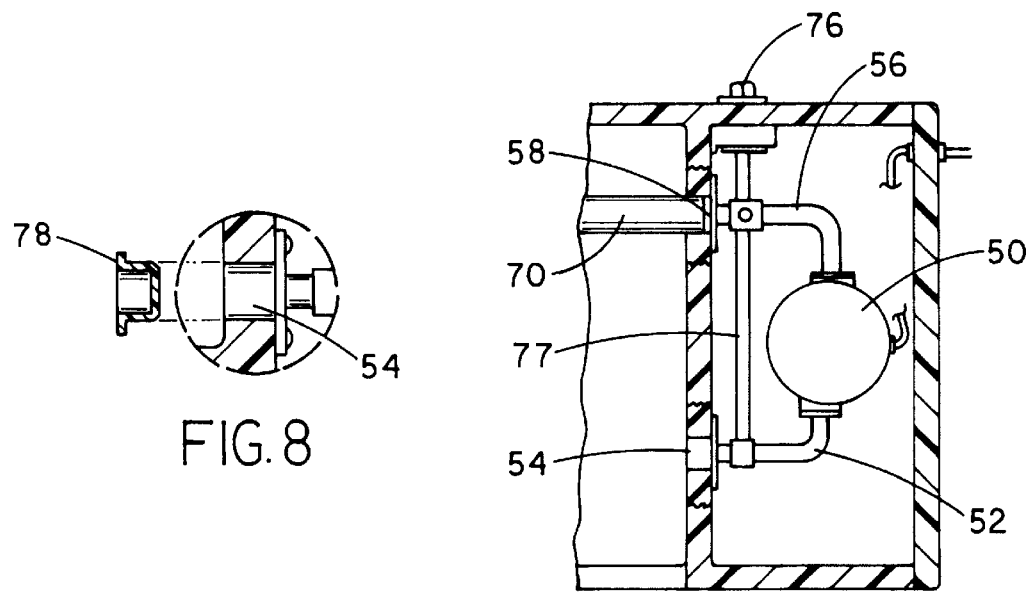
FIG. 7 is a schematic top plan view taken along line 7—7 of the present invention.

With reference now to the drawings, and in particular to FIGS. 1 through 6 thereof, a new hand and finger nail wash unit embodying the principles and concepts of the present invention and generally designated by the reference numeral 10 will be described.

As best illustrated in FIGS. 1 through 6, the hand and finger nail wash unit 10 generally comprises a housing having a front side 12, a back side 14, a top side 16, a first opposing wall 18 and a second opposing wall 20. The opposing walls are substantially parallel to each other, and each of the opposing walls are oriented substantially perpendicular to the front and back sides of the housing. The housing has a bottom portion 22, preferably wherein a distal side 26 of the bottom portion has a relatively thicker cross-sectional thickness than a proximate side 28 cross sectional thickness of the bottom portion such that any liquid within the housing flows toward the proximate side of the housing. Preferably, four legs 24 are on a bottom surface of the bottom portion of the housing.

A compartment 30 in the housing holds a water pump. A vertical wall 32 within an interior of the housing and the first opposing wall 18 form the compartment. The vertical wall is oriented substantially parallel to the opposing walls, wherein the compartment is separated from a remainder of the housing such that the compartment is substantially water-tight.

An aperture 34 is located in the front side for access to an interior of the housing. Preferably, the aperture extends into the top side and the front side of the housing. The aperture is defined by a pair of edges 36 in the vertical wall of the compartment, an edge in the second opposing wall 37, a first horizontal edge 38 in the front side at a height approximately one half of a height of the front side, and a second horizontal edge 39 in the top side at an approximate midpoint of the front side and the back side.

A dispenser means for dispensing cleansing agents is mounted on the back side 14 of the housing such that the cleansing agents are dispensed through the aperture 34. Preferably, the dispenser is a pump dispenser 40. Ideally the top side of the housing has a depression 41 therein to facilitate addition of a cleansing agent into the interior of the housing.

Preferably, a brush 42 for cleaning nails is mounted on an inside surface the bottom portion of the housing. A fastener means, preferably a screw 43, is used attaching the brush to the bottom portion.

A water pump is used for pumping water through the housing. A water pump casing 50 is mounted in the compartment 30. The water pump casing contains an electrically operated water pump. An intake pipe 52 receives water from the housing and is fluidly connected to the water pump casing. The intake pipe is fluidly connected with a first bore 54 in the vertical wall 32. The first bore is located adjacent to the bottom portion 22 of the housing. An outlet pipe 56 for directing water from the water pump casing into the housing is fluidly connected to the water pump housing. The outlet pipe is fluidly connected to a second bore 58 in the vertical wall 32. The second bore is substantially adjacent to the back side 14 of the housing. An actuator means is used for turning the water pump on. The actuator is mounted on a top surface 16 of the top side of the housing and is operatively coupled to the water pump 50 wherein the actuator means comprises a switch operated by a push button 60. A power cord 61 is operatively coupled to the water pump and extends through a bore 62 in the compartment.

A delivery pipe 70 for delivering water into the housing is fluidly connected to the second bore 58. The delivery pipe extends a length of the housing between the second opposing wall 20 and the vertical wall 32 and is oriented substantially perpendicular to the opposing walls. The delivery pipe has bores 72 therein, wherein water is directed out of the bores.

A pressure control valve 73 is used for controlling water pressure out of the bores. The valve is in communication with the outlet pipe 56. The valve has a control knob 74 extending upwardly away from the outlet pipe. The knob extends through a bore in the top side of the housing.

In a second embodiment, the housing further contains a drain hole 75 for draining the housing. The drain hole is located in the back side 14 of the housing adjacent to the bottom portion 22 of the housing.

In an another embodiment, the housing further contains an external water supply inlet 76 for using an external water supply. The external water supply inlet is in the compartment 30 in the back side 14 of the housing. A water supply pipe 77 delivers water from the external water supply pipe to the intake pipe 52. The water supply pipe is in fluid communication with the external water inlet and the intake pipe.

In use, the user places water in the interior of the housing through the aperture 34 to a height covering the pipe 70. The pump is turned on with the push button 60 and water is drawn through the intake pipe 52 and forced out the outlet pipe 56. The water enters the delivery pipe 70, which has bores in it. Preferably the bores are angled to spray the water toward the bottom portion to ensure water is not ejected out of the housing. The water is ejected out of the bores 72 at high pressure. A pressure control valve 74 can moderate the pressure. A user can use higher pressure when cleaning non-water-soluble material from hands such as grease. A brush 42 can be included for scrubbing hands and nails while using the apparatus. A dispenser 40 is employed to deliver cleaning agents into the water. Once the user is done, the pump is turned off and the water can be used until it becomes dirty at which time it can be dumped out by turning the housing upside down.

In a second embodiment, a drain 75 is used in combination with an external water supply. The external water supply is attached to an external water supply inlet 76. The inlet delivers water to the pump. The water can be continuous and allowed to drain out of the drain 75 or, the drain can be plugged to allow the housing to fill with water and then turning the external supply off and using only the water contained in the housing. If the user chooses to use a continuous water supply, a plug 78 can be used to stop water from entering the intake pipe from the housing.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. An automatic washer for cleaning cuticles and underneath fingernails, said washer comprising:

a housing, said housing having a front side, a back side, a top side and a first opposing wall and a second opposing wall, said housing having a bottom portion;

a compartment in said housing for holding a water pump, said compartment being formed by a vertical wall within an interior of said housing and said first opposing wall;

an aperture in said front side for access to an interior of said housing;

a brush for cleaning nails, said brush being mounted on an inside surface of said bottom portion of said housing;

a water pump for pumping water, said water pump being in said compartment, said water pump having an intake pipe for receiving water from said housing, said intake pipe being fluidly connected with a first bore in said vertical wall, said water pump having an outlet pipe for directing water from said pump into said housing, said outlet pipe being fluidly connected to a second bore in said vertical wall; and a delivery pipe for delivering water into said housing, said delivery pipe being fluidly connected to said second bore, said delivery pipe having bores therein, wherein water is directed out of said bores.

2. The automatic washer for cleaning cuticles and underneath fingernails of claim 1, said washer further comprising:

wherein a distal side of said bottom portion has a relatively thicker cross-sectional thickness than a proximate side cross sectional thickness of said bottom portion such that any liquid within said housing flows toward said proximate side of said housing.

3. The automatic washer for cleaning cuticles and underneath fingernails of claim 1, further comprising:

wherein said compartment is separated from a remainder of said housing such that said compartment is substantially watertight.

4. The automatic washer for cleaning cuticles and underneath fingernails of claim 1, wherein said aperture further comprises:

said aperture extending into said top side of said housing, wherein said aperture is defined by an edge in said front side and said top side adjacent to said vertical wall of said compartment, an edge in said front side and said top side adjacent to said second opposing wall, a horizontal edge in said front side at a height approximately one half of a height of said front side, and a horizontal edge in said top side at an approximate midpoint of said front side and said back side.

5. The automatic washer for cleaning cuticles and underneath fingernails of claim 1, and further comprising:

a dispenser means for dispensing cleansing agents, said dispenser means being mounted on said back side of said housing such that said cleansing agents are dispensed through said aperture.

6. The automatic washer for cleaning cuticles and underneath fingernails of claim 1, and further comprising:

a brush for cleaning nails, said brush being mounted on an inside surface said bottom portion of said housing; and a fastening means for attaching said brush to said bottom portion.

7. The automatic washer for cleaning cuticles and underneath fingernails of claim 1, wherein said water pump includes:
   a water pump casing, said water pump casing being mounted in said compartment, said water pump casing containing an electrically operated water pump therein;
   wherein said intake pipe is fluidly connected to said water pump casing, wherein said first bore is located adjacent to said bottom portion of said housing;
   wherein said outlet pipe is fluidly connected with said water pump housing, wherein said second bore is substantially adjacent to said back side of said housing;
   an actuator means for turning said water pump on, said actuator being mounted on a top surface of said top side of said housing, said actuator means being operatively coupled to said water pump wherein said actuator means comprises a switch operated by a push button; and
   a power cord operatively coupled to said water pump, said power cord extending through a bore in said compartment.

8. The automatic washer for cleaning cuticles and underneath fingernails of claim 7, further including:
   a pressure control valve for controlling water pressure out of said bores, said valve being in communication with said outlet pipe, said valve having a control knob, said control knob extending upwardly away from said outlet pipe, said knob extending through a bore in said top side of said housing.

9. The automatic washer for cleaning cuticles and underneath fingernail of claim 1, further comprising:
   a drain hole for draining said housing, said drain hole being located in said back side of said housing adjacent to said bottom portion of said housing.

10. The automatic washer for cleaning cuticles and underneath fingernails of claim 9, further comprising:
    an external water inlet for using an external water supply, said external water inlet being in said compartment in said back side of said housing;
    a water supply pipe for delivering water from said external water supply to said intake pipe, said water supply pipe being in fluid communication with said external water inlet and said intake pipe.

11. An automatic washer for cleaning cuticles and underneath fingernails, said washer comprising:
    a housing, said housing having a front side, a back side, a top side and a first opposing wall and a second opposing wall, said opposing walls being substantially parallel to each other, each of said opposing walls being oriented substantially perpendicular to said front side and said back side of said housing, said housing having a bottom portion, wherein a distal side of said bottom portion has a relatively thicker cross-sectional thickness than a proximate side cross sectional thickness of said bottom portion such that any liquid within said housing flows toward said proximate side of said housing;
    four legs on a bottom surface of said bottom portion of said housing;
    a compartment in said housing for holding a water pump, said compartment being formed by a vertical wall within an interior of said housing and said first opposing wall, said vertical wall being oriented substantially parallel to said opposing walls, wherein said compartment is separated from a remainder of said housing such that said compartment is substantially watertight;
    an aperture in said front side for access to an interior of said housing, said aperture extending into said top side and said front side of said housing, wherein said aperture is defined by an edge in said front side and said top side adjacent to said vertical wall of said compartment, an edge in said front side and said top side adjacent to said second opposing wall, a horizontal edge in said front side at a height approximately one half of a height of said front side, and a horizontal edge in said top side at an approximate midpoint of said front side and said back side;
    a dispenser means for dispensing cleansing agents, said dispenser means being mounted on said back side of said housing such that said cleansing agents are dispensed through said aperture;
    a brush for cleaning nails, said brush being mounted on an inside surface said bottom portion of said housing;
    a screw for attaching said brush to said bottom portion;
    a water pump for pumping water, said water pump comprising:
       a water pump casing, said water pump casing being mounted in said compartment, said water pump casing containing an electrically operated water pump therein;
       an intake pipe for receiving water from said housing, said intake pipe being fluidly connected to said water pump casing, said intake pipe being fluidly connected with a first bore in said vertical wall, said first bore being located adjacent to said bottom portion of said housing;
       an outlet pipe for directing water from said water pump casing into said housing, said outlet pipe being fluidly connected with said water pump housing, said outlet pipe being fluidly connected to a second bore in said vertical wall, said second bore being substantially adjacent to said back side of said housing;
       an actuator means for turning said water pump on, said actuator being mounted on a top surface of said top side of said housing, said actuator means being operatively coupled to said water pump wherein said actuator means comprises a switch operated by a push button; and
       a power cord operatively coupled to said water pump, said power cord extending through a bore in said compartment;
    a delivery pipe for delivering water into said housing, said pipe being fluidly connected to said second bore, said delivery pipe extending a length of said housing between said second opposing wall and said vertical wall, said delivery pipe being oriented substantially perpendicular to said opposing walls, said delivery pipe having bores therein, wherein water is directed out of said bores; and
    a pressure control valve for controlling water pressure out of said bores, said valve being in communication with said outlet pipe, said valve having a control knob, said control knob extending upwardly away from said outlet pipe, said knob extending through a bore in said top side of said housing.

12. The automatic washer for cleaning cuticles and underneath fingernail of claim 11, further comprising:

a drain hole for draining said housing, said drain hole being located in said back side of said housing adjacent to said bottom portion of said housing.

13. The automatic washer for cleaning cuticles and underneath fingernails of claim 12, further comprising:

an external water inlet for using an external water supply, said external water inlet being in said compartment in said back side of said housing;

a water supply pipe for delivering water from said external water supply to said intake pipe, said water supply pipe being in fluid communication with said external water inlet and said intake pipe.

* * * * *